US006514519B1

(12) United States Patent
Nagler

(10) Patent No.: US 6,514,519 B1
(45) Date of Patent: Feb. 4, 2003

(54) EDELFOSIN FOR THE TREATMENT OF BRAIN TUMORS

(75) Inventor: Apollonia Nagler, Grünwald (DE)

(73) Assignee: Med-Mark Pharma GmbH, Oberhaching (DE)

( * ) Notice: Subject to any disclaimer, the term of this patent is extended or adjusted under 35 U.S.C. 154(b) by 0 days.

(21) Appl. No.: 09/700,903

(22) PCT Filed: May 11, 1999

(86) PCT No.: PCT/EP99/03241

§ 371 (c)(1),
(2), (4) Date: Jan. 25, 2001

(87) PCT Pub. No.: WO99/59599

PCT Pub. Date: Nov. 25, 1999

(30) Foreign Application Priority Data

May 19, 1998 (DE) .......................................... 198 22 509

(51) Int. Cl.$^7$ ............................................... A61K 47/00
(52) U.S. Cl. ........................ 424/439; 424/400; 424/464
(58) Field of Search .................................. 424/400, 439

(56) References Cited

U.S. PATENT DOCUMENTS 5,925,669 A * 7/1999 Katz et al. .................. 514/449
6,235,729 B1 * 5/2001 Chen et al. .................. 514/176

OTHER PUBLICATIONS

W. J. Zeller et al., "Interstitial chemotherapy of experimental gliomas", *Cancer Treatment Reviews*, 17:2–3:183–189 (Sep. 1990).
Olav Engebraaten et al., "Effect of alkyl–lysophospholipid on glioblastoma cell invasion into fetal rat brain tissue in vitro", *Cancer Research*, 51(6): 1713–1719 (1991).
Wolfgang, E. Berdel et al., "Cytotoxicity of alky–lysophospholipid derivatives and low–alkyl–cleavage enzyme activities in rat brain tumor cells", *Cancer Research*, 43(2):541–545 (1983).
Wolfgang E. Berdel et al., "Cytoxic effects of alky–lysophospholipids in human brain tumor cells", *Oncology*, 41(2):140–145 (1984).
Clemens Unger et al., "Blood–brain barrier and penetration of cytostatics", *Klin. Wochenschr*, 63(12):565–571 (1985).

* cited by examiner

*Primary Examiner*—Thurman K. Page
*Assistant Examiner*—Claresse Evans
(74) *Attorney, Agent, or Firm*—Fulbright & Jaworski

(57) ABSTRACT

Octadecyl-2-methyl-sn-glycero-3-phosphocholine (edelfosine) is suitable for the treatment of brain tumors and can therefore be used to produce a drug for the treatment of brain tumors which can also be administered orally.

7 Claims, No Drawings

EDELFOSIN FOR THE TREATMENT OF BRAIN TUMORS

The invention relates to edelfosine (INN; 1-octadecyl-2-methyl-sn-glycero-3-phosphocholine, frequently also referred to as ET18OCH3) for the treatment of primary and secondary brain tumors originating from solid and nonsolid tumors.

Permanent cure of a malignant brain tumor is, according to the present state of knowledge, impossible, i.e. there are at present no curative therapeutic approaches to malignant gliomas. The aim is always individual treatment taking account of any losses of function by surgical procedures and a prolongation of the survival time with the best possible quality of life.

The incidence of brain tumors is continuing to increase and becomes more marked as people age. Thus, for example, the average incidence is 1.8/100,000 people 15–24 years of age but about 18.4/100,000 of those 65–79 years of age. The age peak is between 55 and 73 years, although increasing numbers of young patients with glioblastomas have been recorded in recent years. The annual incidence of a primary brain tumor in Germany is about 7000 people, of whom most die within the first year. Despite surgery and irradiation, the people survive on average for only 11 months. The tumor has by then become so large, and such large amounts of fluids have escaped that the brainstem is crushed and functions important to life fail.

The tumors which occur most commonly originate from astrocytes, ependymocytes and oligodendrocytes. The prognosis of brain tumors in principle is poor. Malignant gliomas are the most widespread brain tumors, and of these in turn gliobastoma multiforme and anaplastic astrocytoma, which together account for about 80% of all malignant gliomas, have the poorest prognosis. Especially with these tumors only partial resection is frequently possible.

The currently available nonsurgical therapeutic options—irradiation and chemotherapy—are all associated with adverse drug reactions, some of which are severe, which represents a limiting factor especially for chemotherapeutic approaches for an increasingly aging population with multiple pathologies.

One of the main problems is, however, the fact that recurrence of these tumors is unavoidable even with, or despite, the use of aggressive therapeutic regimen. Long-term therapy with chemotherapeutics is not possible because of the toxicity of these substances, and repeated use is not worthwhile because the response rates then approach zero. The limit for radiation exposure is likewise reached relatively quickly if it is intended to treat even the primary tumor effectively. Thus, the situation is still such that after completion of the first therapeutic regimen it is necessary to "wait" until there has been renewed occurrence. Even the most frequent checks are unable to alter this in any way.

In principle, primary brain tumors are categorized as tumors for which even now there are no effective, curative therapeutic approaches. In a very recent decision in Italy, malignant gliomas were even categorized as an orphan drug indication because effective therapeutic approaches are lacking. An additional factor is that of the approx. 2,000,000 cancers reported annually around the world, 800,000—which is 40%—are a priori resistant to chemotherapy, and thus real alternative therapies are still required even more urgently than ever.

Therapeutic Approaches Currently in Use

Malignant brain tumors are among the most malignant tumors of all; their prognosis is unfavorable. Even with a combination of surgery, irradiation and chemotherapy, the survival time from the date of diagnosis of patients with highly differentiated gliomas is usually less than one year.

Surgical removal of a malignant tumor with total removal of the tumor, i.e. with the objective of cure, is always the therapy of choice. However, inoperability frequently pertains; thus, for example, of all astrocytomas diagnosed, only a little more than 20% are operable, and only partial resection is possible in most cases.

The only possibility remaining is therefore often radioactive irradiation, which is, however, likewise associated with side effects and has the disadvantage of a therapy which can be used only locally. Most tumor foci have an edge with distinct margins which can be visualized even by computed tomography (CT) or magnetic resonance imaging (MRI), so that inevitably a considerable portion of healthy tissue must be included in the area to be irradiated. The tolerance or lack of resistance of this healthy tissue is therefore the limiting factor. However, since the local treatment modalities are becoming increasingly aggressive, an increase in radiation-induced damage must be assumed. This comprises either 1. acute reactions: development of an edema within a few hours, accompanied by headaches, nausea/vomiting, somnolence, fever, deterioration in neurological symptoms; 2. early delayed reactions: a few weeks to 4 months after irradiation owing to temporary demyelinization or radiation-induced change in the permeability of the capillaries; is manifested by temporary neurological deterioration, somnolence and focal (focal=originating from a focus) encephalopathy; 3. late reactions: several months to years after the treatment. These are in fact the most severe and are manifested by strokes, neuropsychological disorders, dementia, atrophy of the cerebral cortex (in up to 39% of patients with whole brain irradiation).

Chemotherapies are in principle used only in the form of an adjuvant therapy, i.e. immediately after surgical removal of the tumor. However, chemotherapy almost always fails for brain tumors because the blood-brain barrier—a natural barrier to toxins and pathogens—prevents the penetration of most drugs into the brain. Although there are some medicines (substances predominantly from the nitrosourea class) able to overcome the blood-brain barrier, their effect is extremely controversial. Correspondingly, it has not yet been possible to establish a standard chemotherapy. The WHO accordingly classifies brain tumors as tumors which are insensitive or only extremely marginally sensitive to cytotoxic treatment.

Even the most recently developed drugs do not denote a genuine advance in the sense of novel molecular therapeutic approaches. The cytostatic carmustine, a nitrosourea derivative, is implanted in the form of medicine-impregnated wafers into the tumor cavity even during the operation but, even then, shows only a moderate effect or none. Apart from this, it can be used only for operable cases. In addition, this cytostatic if given systemically has, as a molecule with a nonselective effect like all known cytostatics, a harmful effect on the body's normal cells, i.e.

its use is associated with corresponding unwanted side effects (such as, for example, genetic damage, pulmonary toxicity, myelosuppression inter alia). This also applies to other cytostatics occasionally used for treating brain tumors, such as "procarbazine", "cyclophosphamide", "vincristine". In many treatment centers, therefore, patients with glioblastomas and poor prognostic criteria are excluded from chemotherapy from the outset.

Because the activity of the known cytostatics is in principle lacking or, at the most, moderate for primary or secondary brain tumors, in the final analysis the question of whether cytotoxic substances are able to overcome the blood-brain barrier or not is purely academic (cf. DeVita & al. 1997, p. 2041).

The object of the invention is therefore to produce a drug for the treatment of brain tumors which has the following advantages:

a) the medicine is able to cross barriers better
b) the pharmacodynamic effect is reproducible
c) there is therapeutic efficacy even in the last resort situation
d) there is no organotoxicity
e) a maximum quality of life is ensured with acceptable adverse drug reactions (ADR)
f) use is simplified, outpatients therapy where possible
g) the duration of therapy is unlimited.

This object is achieved according to the invention by the use of edelfosine as active ingredient for a drug for the treatment of brain tumors. Edelfosine can be employed for this purpose in the L form, the D form or as racemate.

Edelfosine has two advantages which make it appear most suitable for use in the therapy of primary (i.e. originating from brain cells) and secondary (that is to say occurring in the brain but not originating from body cells intrinsic to the brain) brain tumors.

On the one hand, the molecule has a strictly selective effect (cf. Hickman 1992, FIG. 7). After uptake into the cells, it displays its cytostatic effect only on the degenerate cells, whereas it is degraded in healthy cells (cf. Magistrelli & al. 1994, Tab. 2). This selectivity means, on the one hand, that the molecule is neither mutagenic (cf. King & al. 1981), nor carcinogenic (cf. Berdel & al. 1983; Berger & al. 1984), nor teratogenic/embryotoxic or chromosome-damaging (cf. Bauchinger & al. 1983). The selective effect of edelfosine also results in the adverse drug reactions caused by the medicine differing very clearly in severity, degree and duration from that of the known cytotoxic chemotherapeutics. Because of this characteristic, therapy with edelfosine can be carried out on outpatients without difficulty.

A problem, which was not solved before the invention, in the treatment of cancer consists of the limited duration of the use of a therapy. The toxicity of the currently available medicines permits use on the one hand only in cycles, and on the other hand only for a limited time. Tumor cells which have "lost" the information for genetically programmed cell death (apoptosis) are, however, de facto immortal. An additional factor is that the medical therapies used now presuppose either a particular receptor status or else a particular stage of the cell cycle. It is thus possible during the therapy period, which is anyway subject to a time limit, to deal effectively only with some of the cells, not all of them.

These problems are solved by the invention. On the one hand, the molecule displays its effect not via receptors (cf. Snyder & al. 1991) ; on the other hand, its effect does not depend on the stage of division of a cell; on the contrary it acts via enzymes which are active in every phase of a cell cycle and essentially must be present.

Because of the demonstrated selectivity of edelfosine, the medicine can be given as continuous therapy over a virtually unlimited period, so that the dividing behavior of the brain tumor cells is permanently influenced. The longest duration of therapy reported to date for a brain tumor patient is now more than 6 years. With a total dose of about 640 g, the patient was able to work until he retired and suffered negligible adverse drug reactions (cf. Table 1, column "Pat."—No. 542 therein). Edelfosine can easily be administered orally, expediently dissolved in a drinkable vehicle. Water-based vehicles are preferably used, for example soups (especially thickened soups), beer, eggnog and other conventional beverages. Milk-based vehicles are also suitable, such as milk, milk substitute, yogurt, kefir and the like.

Another advantage is that edelfosine can be employed even for chemotherapy-resistant tumors because it has a completely different mechanism of action which, in contrast to the DNA-interactive cytostatics, acts primarily on the tumor cell membrane and intervenes in the cells' signaling chain. This leads to inhibition of important enzymes, for example phospholipase C, protein kinase C, resulting in the cancer cell no longer being able to divide. Edelfosine also brings about reinduction of apoptosis (cf. Mollinedo & al. 1993); cells influenced in this way lose their "immortality status" as cancer cell.

Pharmacodynamic Effect and Therapeutic Efficacy in vivo in Humans

After completion of the animal experimental part of drug development, the tolerability, pharmacokinetics and pharmacodynamics of a medicine are tested and investigated (testing of absorption, distribution in the body, degradation products, excretion) in phase I studies on humans. However results obtained thereby do not allow conclusions to be drawn about the therapeutic efficacy of a medicine. This information can be obtained only after carrying out phase II studies.

The patients which are listed below in Table 1, with their status before and after treatment, were treated with edelfosine in the phase II study. It is important to emphasize in this connection that virtually all the patients have previously been treated or were from the outset untreatable (inoperable tumors). All the patients were treated with an average of 300 mg of edelfosine/day (range of variation between 50 and 600 mg). For this purpose, the lyophilizate was dissolved in water and added to a carrier medium which had a fat content of at least 3–3.5% and/or a comparable protein content. The carrier medium/active ingredient mixture is drunk in different dose levels/portion, which differed from patient to patient, distributed over the day. Administration is accordingly oral; the treatment is entirely on an outpatient basis, unless the clinical picture makes admission to hospital unavoidable.

TABLE 1

Results of the clinical phase II study with edelfosine

| | Status before starting edelfosine therapy | | | Previous treatment | | | | Status after starting edelfosine therapy | |
|---|---|---|---|---|---|---|---|---|---|
| Pat. | Tumor type | Age | KI% | OP | Rad. | Chemo | Tumor activity | Result of therapy | Survival time |
| 738 | Astrocytoma | 48 | 55 | x | — | — | Progression | No further progression | 495 days |
| 863 | Astrocytoma | 32 | 60 | x | x | — | Progression | Progression | 130 days |
| 602 | Astrocytoma II | 49 | 75 | x | x | — | Progression | No further progression (clin.) | 197 days |
| 546 | Astrocytoma II | 32 | 70 | x | x | — | Progression | No further progression | 753 days |
| 146 | Astrocytoma II | 53 | 55 | x | — | — | Progression | No further progression (clin.) | 98 days |
| 807 | Astrocytoma II | 36 | 60 | — | x | — | Progression | No further progression (clin.) | 169 days |
| 144 | Astrocytoma II/III | 36 | 80 | 2x | x | — | Progression | No further progression | 412 days |
| 681 | Astrocytoma III | 57 | 75 | 2x | 2x | — | Progression | Progression | 138 days |
| 671 | Astrocytoma III | 40 | 100 | x | x | — | Progression | No further progression | 270 days |
| 834 | Astrocytoma III | 30 | 70 | 3x | — | — | Progression (clin.) | Progression | 1769 days |
| 576 | Astrocytoma III | 34 | 70 | 2x | — | — | Progression | Unclear | 90 days |
| 284 | Ependymoblastoma | 34 | 60 | 9x | x | — | Progression | Progression | 196 days |
| 511 | Glioblastoma | 28 | 50 | 3x | x | x | Progression | No further progression | 619 days |
| 746 | Glioblastoma | 62 | 90 | x | x | — | Progression | No further progression | 188 days |
| 692 | Glioblastoma | 53 | 50 | x | 2x | — | Progression | Progression | 92 days |
| 247 | Glioblastoma | 38 | 90 | x | x | — | Progression | No further progression | 2808 days |
| 865 | Glioblastoma | 55 | 60 | 2x | x | — | Progression (clin.) | No further progression | 338 days |
| 852 | Glioblastoma IV | 48 | 80 | 2x | x | — | Progression | Progression | 143 days |
| 849 | Glioblastoma IV | 22 | 20 | — | x | — | Progression | No further progression (clin.) | 266 days |
| 831 | Glioblastoma IV + Gliosarcoma | 58 | 80 | x | x | — | Progression | No further progression | 203 days |
| 225 | Glioblastoma (Ø histol.) | 50 | 85 | — | x | x | Progression | No further progression (clin.) | 372 days |
| 207 | Glioblastoma (Ø histol.) | 60 | 90 | — | — | — | Progression | Progression | 105 days |
| 399 | Glioblastoma multiforme | 49 | 70 | — | x | — | Progression | No further progression | 301 days |
| 390 | Glioblastoma multiforme | 60 | 70 | 2x | x | x | Progression (clin.) | No further progression | 270 days |
| 598 | Glioblastoma multiforme | 21 | 60 | 2x | 1x | 6x | Progression | Progression | 221 days |
| 226 | Glioblastoma multiforme | 58 | 80 | 2x | x | 3x | Progression | No further progression | 242 days |
| 214 | Glioblastoma multiforme | 53 | 80 | 2x | — | — | Progression | Progression | 90 days |
| 716 | Glioblastoma multiforme | 34 | 60 | 2x | x | — | Progression | Progression | 140 days |
| 514 | Glioblastoma multiforme | 23 | 80 | x | 2x | — | Progression | Progression/clin. stable | 1165 days |
| 147 | Glioblastoma multiforme | 67 | 90 | x | x | — | Progression | No further progression | 266 days |
| 541 | Glioblastoma multiforme | 52 | 80 | x | x | 3x | Progression | No further progression (clin.) | 198 days |
| 2 | Glioblastoma multiforme | 68 | 80 | x | x | — | Progression | No further progression | 379 days |
| 454 | Glioblastoma multiforme | 22 | 70 | x | x | 2x | Progression | No further progression | 361 days |
| 896 | Gliosarcoma | 36 | 50 | 2x | x | — | Progression | No further progression | 110 days |
| 728 | Oligoastrocytoma II | 47 | 55 | x | x | — | Progression | No further progression (clin.) | 270 days |
| 241 | Oligoastrocytoma IV | 49 | 70 | x | x | — | Progression | No further progression | 1602 days |
| 612 | Anaplastic oligodendroglioma | 33 | 60 | x | x | — | Progression | No further progression | 404 days |
| 286 | Anaplastic oligodendroglioma | 46 | 60 | x | x | — | Progression | No further progression | 193 days |
| 327 | Oligodendroglioma III | 36 | 90 | 4x | x | — | Progression | No further progression | 573 days |

TABLE 1-continued

| 542 | Oligodendroglioma III/IV | 54 | 90 | x | x | x | Progression | No further progression | 2141 days |
| 894 | Oligodendroglioma IV | 37 | 35 | — | x | x | Progression | No further progression | 572 days |

The data in this table are explained in detail below:
Distribution according to type of tumor
Astrocytomas                         N = 11 (26.8%)
Glioblastomas incl. gliosarcomas     N = 20 (48.8%)
Oligoastrocytomas/dendrogliomas      N = 7 (17.1%)
Other tumors/unclear histology       N = 3 (7.3%)

(but brain-intrinsic tumors)
                                     N = 41 (100%)
(cf. Table 1, column "Type of tumor")

Age

The treated patients (N=23 male, N=18 female) had an average age of 43.9 years with a minimum of 21 years and a maximum of 69 years. Of these, N=18 patients (about 44%) were less than 40 years of age, N=18 (about 44%) were between 40 and 59 years old and only N=5 patients (about 12%) were older than 60 years (cf. Table 1, column "Age").

Karnofsky Index/general Condition(KI%)

In patients with brain tumors, the Karnofsky index is an important prognostic factor, as a measure of the clinical condition or general condition, which already decides about treatment or nontreatment with cytostatics. It is generally recommended that an adjuvant (NB) chemotherapy be used only if the Karnofsky index is ≧70% (cf. Bogdahn & al. 1995). The general condition is normally measured by the internationally used Karnofsky scale.

The Karnofsky index for the treated edelfosine patients averaged 69.6%, but varied very widely, with a range of variation of 20–100%. Nevertheless, N=16 patients (about 39%) had a Karnofsky index of <70%, N=5 patients (about 12%) even had a Karnofsky index of ≦50% (cf. Table 1, column "KI%"). If the general rule of treating only when the Karnofsky index is ≧70 had been obeyed, almost 39% of these patients, with an average survival time of about 260 days (cf. Table 1, column "Survival time"), which is still more than 8 months, would not have been treated at all. The range of variation in this connection was 90–619 days, with the maximum gain in survival time correspondingly being >20 months.

Previous Treatment

The number and duration of previous treatments before the start of therapy with a medicine are crucial for assessing the therapeutic efficacy=survival time and quality of survival; the survival time is in such cases always measured from the time at which the therapy with a medicine is started. The time which has elapsed from diagnosis until the start of treatment initially plays no direct part in this. However, it must be taken into account when the survival time of a last resort therapy (as edelfosine in this case) is compared with that of therapies which are usually started immediately after diagnosis (this is the case for chemotherapy and radiation studies).

About 85% of the patient population treated with edelfosine had received several previous treatments; i.e. more than one type of treatment from the possibilities of surgery, irradiation or chemotherapy had already been used before starting the edelfosine therapy. Alternative therapeutic methods (mistletoe, hyperthermia etc.) were not evaluated.

Broken down according to the surgery, irradiation and chemotherapy, this means that for about 85% of the patients a recurrence or residual tumor after unsuccessful surgery (including multiple) led to taking up the treatment with edelfosine. Irradiation (including multiple) likewise applied to about 85% of all the patients; chemotherapy had been used for about 22% of the patients before the edelfosine therapy was started.

For virtually all the patients, a tumor which continued to grow after all the therapies used led to the edelfosine therapy, i.e. the tumor was progressive (cf. Table 1, column "Tumor activity"). The specification of "clinical" progression means in this connection that the tumor was progressive on the basis of deteriorating clinical symptoms (for example increase in headaches, congestion in the head, dizziness, tendency to fall, neurological symptoms in general), but no objective study (for example CT) was available for comparison.

Pharmacodynamic Effect (Result of Therapy)

The pharmacodynamic effect, i.e. the effect of a medicine directly on the tumor, is normally measured 2 months after starting a therapy. This pharmacodynamic effect is defined differently depending on which class the substance belongs to (that is to say cytostatic, hormone product, immunomodulator etc.). Edelfosine is a phenotype modifier/biological response modifier and thus does not lead directly to direct killing of a cell but, on the contrary, to inhibition of its division, to reinduction of apoptosis and/or to differentiation into a "normal" cell. The aim of therapy is accordingly a cessation of tumor growth (no change).

The stabilization of tumor development was found in a high percentage of the treated patients with a brain tumor (see Table 1, column "Result of therapy").

Objectively assessed by an imaging study after 2 months of therapy, about 56% of the treated patients were found to have cessation of tumor growth (NC=no change). For a further approx. 14% although there are no objective study was done, a stabilization was found on the basis of the clinical symptoms (cNC=clinical no change). This is often the only aim of therapy to be achieved in a palliative situation where a cure is no longer possible; however, a therapist must in any event confine himself to a purely palliative treatment in cases of inoperable, recurrent or metastasized tumors. If this alleviation (palliation) is moreover achieved with substantial absence of adverse drug reactions (=side effects), then even clinical stabilization corresponds to a real gain of therapy.

In about 24% of all the treated patients the tumor was still progressive after 2 months, there being a discrepancy in the findings in 2% inasmuch as a clinical stabilization/improvement was found although the tumor was progressive according to imaging methods.

During phase II studies, in accordance with requirements the adverse drug reactions (ADR) were also investigated. The result is shown in Table 2:

TABLE 2

| Grading | 0 | Grade 1 | | | Grade 2 | | | Grade 3 | | | Grade 4 | | | ∅ | |
|---|---|---|---|---|---|---|---|---|---|---|---|---|---|---|---|
| Symptom | | yes | ? | no | yes | ? | no | yes | ? | no | yes | ? | no | assessment | Courses |
| Appetite | 123 | 4 | 5 | 4 | 1 | 2 | 1 | 2 | 2 | 4 | — | — | 1 | 1 | 150 |
| Nausea/vomiting | 121 | 12 | 5 | 1 | 2 | 6 | 8 | — | — | 2 | — | — | — | 2 | 159 |
| Diarrhea | 142 | 5 | 1 | — | 1 | — | 1 | — | — | — | — | — | — | — | 150 |
| Constipation | 143 | 3 | 3 | 1 | — | — | — | — | — | — | — | — | — | — | 150 |
| Stomatitis | 149 | — | — | — | — | — | — | — | — | — | — | — | — | — | 149 |
| Fever | 142 | — | — | 1 | — | — | 7 | — | — | — | — | — | — | — | 150 |
| Infection | 146 | — | — | 3 | — | — | 1 | — | — | — | — | — | — | — | 150 |
| Dyspnea | 141 | — | — | 4 | — | — | 3 | — | — | 1 | — | — | 1 | — | 150 |
| Allergy | 151 | — | — | — | — | — | — | — | — | — | — | — | — | — | 151 |
| Skin changes | 145 | — | — | — | — | — | — | — | — | — | — | — | 3 | — | 148 |
| Alopecia | 125 | — | 1 | 3 | — | — | 1 | — | — | 3 | — | — | 16 | — | 149 |
| CNS toxicity | 133 | — | 1 | 1 | — | — | — | — | — | — | — | — | — | — | 135 |
| Periph. neurop. | 131 | — | — | 18 | — | — | — | — | — | — | — | — | — | — | 149 |
| Heart failure | 150 | — | — | — | — | — | — | — | — | — | — | — | — | — | 150 |
| Arrhythmia | 145 | — | — | 5 | — | — | — | — | — | — | — | — | — | — | 150 |
| Hematuria | 149 | — | — | — | — | — | — | — | — | — | — | — | — | — | 149 |
| Hemorrhages | 148 | — | — | 2 | — | — | — | — | — | — | — | — | — | — | 150 |
| Pain | 133 | — | — | 7 | — | — | 5 | — | — | 3 | — | — | — | 1 | 149 |

List of the adverse drug reactions (ADR) reported during edelfosine therapy
Grade 0 = no symptom reported
Grade/yes = ADR caused by edelfosine
Grade/? = ADR possibly caused by edelfosine
Grade/no = ADR not caused by edelfosine
∅ assessment = no assessment recorded
For assessment of the severity = gradings 1–4 (mild to severe)

Explanation

The grading of the symptoms as transferred to the case report forms took place in accordance with the internationally used WHO classification.

The assessment "yes" means that a symptom is caused by the medicine. The assessment "?" (doubtful) means that the cause of the reported symptom is unclear; the assessment "no" means that the symptom is unambiguously caused by the disease and not by the medicine.

Particular pathological states are often associated with very particular symptoms so that an unambiguous assessment of the cause of a symptom is not always possible. "Nausea/vomiting" are, particularly with primary brain tumors and depending on the location of the tumor, often tumor-induced and not medicine-induced.

The ADRs caused by the edelfosine therapy typically have a short duration. ADRs often appear in the first two months of the therapy and then disappear entirely. However, in every case the observed symptoms are reversible within a very short time (hours). It should, however, be emphasized that all the reported ADRs are always without a pathological correlate. Thus, for example, appropriate investigations of the esophagus and of the stomach (esophagoscopy, gastroscopy) in patients who had suffered from nausea/vomiting ("gastric pressure") during edelfosine therapy showed no pathological findings at all. Many patients experienced absolutely no ADRs due to the therapy. Pat. No. 542 suffered no ADRs at all during intake of edelfosine lasting almost 6 years, while Pat. No. 247 complained of "nausea/loss of appetite" during the therapy, but is still doing this, i.e. many years after completion of the therapy (has now survived until the 8th year).

There is definitely no cumulative toxicity even after several years of uninterrupted therapy, nor is this to be expected on the basis of the selective mechanism of action.

This means that, in contrast to a treatment of the known type which can be carried only in hospital, the edelfosine therapy according to the invention ensures a very high quality of life.

Therapeutic Efficacy

The therapeutic efficacy is measured in particular in the form of the quality of survival and the survival time. It is not now disputed that although a measurement of a pharmacodynamic effect alone (complete remission/partial remission/no change) is important in studies of therapy, it need not have any value for the patient per se. This applies very particularly to the palliative situation, in which a cure is no longer possible. The relation between a possible effect of the therapy and the side effects of a treatment must then be examined particularly carefully because the side effects of a medicine have a disproportionately greater weight with palliative therapy than with curative therapy. The aim of palliation is without doubt also the attempt to prolong the survival time and/or improve the quality of life, ideally a combination of the two.

The survival time is measured from the start of therapy with a medicine. The state of the art survival time data reported in the literature for the treatment of brain tumors are usually based on either adjuvant treatment of patients, that is to say directly after surgical removal of a tumor, or else on treatment immediately after making the diagnosis.

The patients treated with edelfosine all had a history of some length, i.e. they had for the most part received multiple previous treatment. For this reason, comparison of the survival data reported in Table 1 (cf. Table 1, column "Survival time") with literature data is very difficult or simply impossible. The data presented in Table 1 on the contrary corresponds to a last resort therapy situation with a survival time which is correspondingly already shortened due to the previous treatment.

Comparison is also difficult because the patients included in the present study were not the usually highly selected ones regularly recruited for clinical studies. On the contrary, every patient for whom the conventional medical treatment options had been exhausted but who still required therapy was treated.

The investigations which were performed revealed that it is immaterial that the metastases located in the brain derived from solid tumors (for example carcinomas of the lung, carcinomas of the breast, colorectal carcinomas etc.) or from non-solid tumors (for example lymphomas, leukemias etc.). It may be mentioned only in passing that patients with brain metastases originating, for example, from a non-small-cell bronchial carcinoma usually have a survival time of 6 months, and brain metastases are normally regarded as a criterion for exclusion from chemotherapy studies.

SOURCES

Bauchinger, M. & al. (1983). Cytogenetic effects of an alkyllysophospholipid derivative in human peripheral lymphocytes exposed in vitro and in vivo. Mutation Research 121: 225 ff.

Berdel, W. E. & al. (1983). Experimental chemotherapy of radiation injury with synthetic lysophospholipid analogs in mice. Radiation Research 94: 166 ff.

Berdel, W. E. & al. (1984). Cytotoxic effects of alkyllysophospholipids in human brain tumor cells. Oncology 41: 140 ff.

Berger, M. R. & al. (1984). Influence of the alkyllysophospholipid ET 18 OCH3 on methylnitrosourea-induced rat mammary carcinomas. Oncology 41: 109 ff.

Berens, M. & al. 1993. Effects of structural modifications of ether lipids on antiproliferative activity against human glioma cell lines. Anticancer Research 13: 401 ff.

Bogdahn, U. & al. (1995). Chapter V-2.19 Maligne Gliome. In: Zeller, W. J. & H. zur Hausen (Hrsg.). Onkologie. Ecomed. Verlag, Landsberg.

Carmustin. Unerwünschte Arzneimittelwirkungen gemäβ aktueller Fachinformation.

De Vita, V. T. & al. (1997). Cancer—Principles & Practice of Oncology. Chapt. 42, Neoplasms of the Central Nervous System. 5th ed., Lippincott-Raven, Philadelphia, N.Y.

Engebraaten, O. & al. (1991). Effect of alkyllysophospholipid on glioblastoma cell invasion into fetal rat brain tissue in vitro. Cancer Research 51: 1713 ff.

Hickman, J. A. (1992). Membrane and Signal Transduction Targets. In: Workman, P. (Ed.), New Approaches in Cancer Pharmacology: Drug Design and Development. Springer Verlag, Berlin.

King, M. & al. (1981). Failure to detect mutagenic effects of anti-tumor akyllysophospholipids. Canc. Lett. 12: 217 ff.

Magistrelli, A. & al. (1994). Fate of 1-O-octadecyl-2-O-methyl-rac-glycero-3-phosphocholine (ET18-OMe) in malignant cells, normal cells and isolated and perfused rat liver. Drug Metabolism and Disposition 23(1): 113 ff.

Mollinedo, F. & al. (1993). Early and selective induction of apoptosis in human leukemic cells by the alkyllysophospholipid ET-18-OCH3. Biochemical and Biophysical Research Communications 192(2): 603 ff.

Synder, F. & al. (1991). Membrane-targeted biochemical effects and the role of cellular differentiation in the selective antitumor actions of alkylmethoxyglycerophosphocholine. In: Honn, K.V. (eds.) Eicosanoids and other bioactive lipids in cancer and radiation injury. Kluwer Acad. Publ., Boston/Dodrecht/London.

WHO (1994). Essential drugs for cancer chemotherapy. Bulletin of the World Health Organization 72(5): 693 ff.

What is claimed is:

1. A method for the treatment of brain tumors, wherein active ingredient 1-octadecyl-2-methyl-sn-glycero-3-phosphocholine is converted into a form suitable for oral administration in a liquid vehicle and administered to a patient having a brain tumor, thereby treating said brain tumor.

2. The method of claim 1, wherein the active ingredient is dissolved in a liquid drinkable carrier material.

3. The method of claim 2, wherein said liquid carrier material contains at least 3% by weight fat, protein, or both fat and protein.

4. The method of claim 2, wherein a water-based beverage is used as said carrier material.

5. The method of claim 4, wherein said water-based beverage is milk.

6. The method of claim 1, wherein the amount of active ingredient is portioned for a daily dose.

7. The method of claim 6, wherein said daily dose is 50 to 600 mg.

* * * * *